United States Patent
Balzum et al.

(10) Patent No.: US 6,911,016 B2
(45) Date of Patent: Jun. 28, 2005

(54) GUIDEWIRE EXTENSION SYSTEM

(75) Inventors: Brian K. Balzum, Plymouth, MN (US); Anthony C. Vrba, Maple Grove, MN (US); Brice L. Shireman, Maple Grove, MN (US); Peter Skujins, Minneapolis, MN (US); Kenneth M. Merdan, Greenfield, MN (US); Daniel J. Gregorich, Grand Forks, ND (US); Pu Zhou, Eden Prairie, MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/925,881

(22) Filed: Aug. 6, 2001

(65) Prior Publication Data

US 2003/0028127 A1 Feb. 6, 2003

(51) Int. Cl.⁷ .............................................. A61M 37/00
(52) U.S. Cl. ...................... 604/95.04; 600/585
(58) Field of Search ........................ 606/108, 159, 606/190, 192, 194, 195, 198; 600/434, 585, 435; 604/95.04, 280, 281, 283, 905

(56) References Cited

U.S. PATENT DOCUMENTS

| | | |
|---|---|---|
| 3,631,848 A | 1/1972 | Muller |
| 4,700,705 A * | 10/1987 | Kensey et al. ............ 606/159 |
| 4,827,941 A | 5/1989 | Taylor et al. |
| 4,846,193 A | 7/1989 | Tremulis et al. |
| 4,875,489 A | 10/1989 | Messner et al. |
| 4,907,332 A | 3/1990 | Christian et al. |
| 4,917,103 A | 4/1990 | Gambale et al. |
| 4,922,923 A | 5/1990 | Gambale et al. |
| 4,958,642 A | 9/1990 | Christian et al. |
| 4,961,433 A | 10/1990 | Christian |
| 4,966,163 A | 10/1990 | Kraus et al. |
| 5,031,636 A | 7/1991 | Gambale et al. |
| 5,109,867 A | 5/1992 | Twyford, Jr. |
| 5,113,872 A | 5/1992 | Jahrmarkt et al. |
| 5,117,838 A | 6/1992 | Palmer et al. |
| 5,133,364 A | 7/1992 | Palermo et al. |
| 5,139,032 A | 8/1992 | Jahrmarkt et al. |
| 5,188,621 A | 2/1993 | Samson |
| 5,191,888 A | 3/1993 | Palmer et al. |
| 5,195,535 A | 3/1993 | Shank |
| 5,195,540 A | 3/1993 | Shiber |
| 5,234,002 A * | 8/1993 | Chan ......................... 600/585 |
| 5,247,942 A | 9/1993 | Prather et al. |
| RE34,466 E | 12/1993 | Taylor et al. |
| 5,267,573 A | 12/1993 | Evans et al. |
| 5,271,415 A | 12/1993 | Foerster et al. |
| 5,275,173 A | 1/1994 | Samson et al. |
| 5,282,478 A | 2/1994 | Fleischhaker, Jr. et al. |
| 5,295,492 A | 3/1994 | Sellers |
| 5,338,301 A | 8/1994 | Diaz |
| 5,339,833 A | 8/1994 | Berthiaume et al. |
| 5,341,817 A | 8/1994 | Viera |

(Continued)

FOREIGN PATENT DOCUMENTS

| | | |
|---|---|---|
| CA | 1307179 | 9/1992 |
| CA | 1323814 | 11/1993 |

(Continued)

OTHER PUBLICATIONS

US 5,197,486, 3/1993, Frassica (withdrawn)

Primary Examiner—Julian W. Woo
Assistant Examiner—Victor Nguyen
(74) Attorney, Agent, or Firm—Crompton, Seager & Tufte LLC

(57) ABSTRACT

Devices and methods for coupling guidewire system components are disclosed. A guidewire system includes a first wire having a first end and a second wire having a second end which may be selectively coupled to the first end of the first wire. Such guidewire systems are useful as guidewire extension systems.

6 Claims, 15 Drawing Sheets

U.S. PATENT DOCUMENTS

| | | | |
|---|---|---|---|
| 5,361,777 A | | 11/1994 | Sellers |
| 5,364,355 A | | 11/1994 | Alden et al. |
| 5,365,942 A | * | 11/1994 | Shank ........................ 600/585 |
| 5,365,944 A | | 11/1994 | Gambale |
| 5,395,336 A | | 3/1995 | Barclay et al. |
| 5,404,886 A | | 4/1995 | Vance |
| 5,404,888 A | | 4/1995 | Kontos et al. |
| 5,415,178 A | | 5/1995 | Hsi et al. |
| 5,421,348 A | | 6/1995 | Larnard |
| 5,441,055 A | | 8/1995 | Ales et al. |
| 5,454,785 A | | 10/1995 | Smith |
| 5,511,559 A | | 4/1996 | Vance |
| 5,513,650 A | | 5/1996 | Johansen |
| 5,542,938 A | | 8/1996 | Avellanet et al. |
| 5,546,958 A | | 8/1996 | Thorud et al. |
| 5,605,163 A | | 2/1997 | Hani |
| 5,617,875 A | | 4/1997 | Schwager |
| 5,651,373 A | | 7/1997 | Mah |
| 5,693,083 A | * | 12/1997 | Baker et al. ................ 623/1.11 |
| 5,701,911 A | | 12/1997 | Sasamine et al. |
| 5,782,776 A | | 7/1998 | Hani |
| 5,788,653 A | | 8/1998 | Lorenzo |
| 5,792,075 A | | 8/1998 | Schwager |
| 5,813,405 A | | 9/1998 | Montano, Jr. et al. |
| 5,813,996 A | | 9/1998 | St. Germain et al. |
| 5,827,241 A | | 10/1998 | Douk et al. |
| 5,830,157 A | | 11/1998 | Foote |
| 5,851,192 A | | 12/1998 | Shimura et al. |
| 5,853,375 A | | 12/1998 | Orr |
| 5,897,567 A | * | 4/1999 | Ressemann et al. ......... 606/159 |
| 5,980,471 A | | 11/1999 | Jafari |
| 5,994,667 A | * | 11/1999 | Merdan et al. ........ 219/121.67 |
| 6,039,700 A | | 3/2000 | Sauter |
| 6,080,117 A | | 6/2000 | Cornelius |
| 6,090,052 A | | 7/2000 | Akerfeldt et al. |
| 6,099,534 A | | 8/2000 | Bates et al. |
| 6,152,914 A | | 11/2000 | Van De Kerkerkhof et al. |
| 6,193,706 B1 | | 2/2001 | Thorud et al. |
| 6,196,980 B1 | | 3/2001 | Akerfeldt et al. |
| 6,217,526 B1 | | 4/2001 | Frassica |
| 6,240,615 B1 | * | 6/2001 | Kimes et al. .................. 29/516 |
| 6,270,476 B1 | * | 8/2001 | Santoianni et al. ...... 604/95.04 |
| 6,322,586 B1 | * | 11/2001 | Monroe et al. ............. 623/1.11 |
| 6,436,056 B1 | * | 8/2002 | Wang et al. ................. 600/585 |
| 6,440,503 B1 | * | 8/2002 | Merdan et al. ............. 427/561 |
| 6,575,920 B2 | * | 6/2003 | Zhou .......................... 600/585 |

FOREIGN PATENT DOCUMENTS

| | | |
|---|---|---|
| EP | 0 160 870 A2 | 11/1985 |
| EP | 0 313 807 A1 | 5/1989 |
| EP | 0 347 035 B1 | 12/1989 |
| EP | 0 367 472 A3 | 5/1990 |
| EP | 0 367 472 A2 | 5/1990 |
| EP | 0 383 159 A1 | 8/1990 |
| EP | 0 566 523 A1 | 10/1993 |
| EP | 0 591 945 A1 | 4/1994 |
| EP | 0 397 055 B1 | 10/1994 |
| EP | 0 689 849 A1 | 1/1996 |
| EP | 0 689 850 B1 | 9/1996 |
| EP | 0 697 899 B1 | 12/1997 |
| EP | 0 815 892 A1 | 1/1998 |
| JP | 2783554 | 1/1990 |
| JP | 8084776 A | 4/1996 |
| JP | 9-51954 | 9/1997 |
| JP | 10-043310 | 2/1998 |
| JP | 11128361 A | 5/1999 |
| JP | 11128362 A | 5/1999 |
| WO | WO 92/18051 | 10/1992 |
| WO | WO 93/03664 | 3/1993 |
| WO | WO 93/03786 | 3/1993 |
| WO | WO 93/13827 | 7/1993 |
| WO | WO 93/14805 | 8/1993 |
| WO | WO 94/11049 | 5/1994 |
| WO | WO 94/25097 | 11/1994 |
| WO | WO 94/26343 | 11/1994 |
| WO | WO 95/08294 | 3/1995 |
| WO | WO 96/29001 | 9/1996 |
| WO | WO 98/26833 | 6/1998 |
| WO | WO 00/45885 | 8/2000 |
| WO | WO 01/39825 | 6/2001 |

* cited by examiner

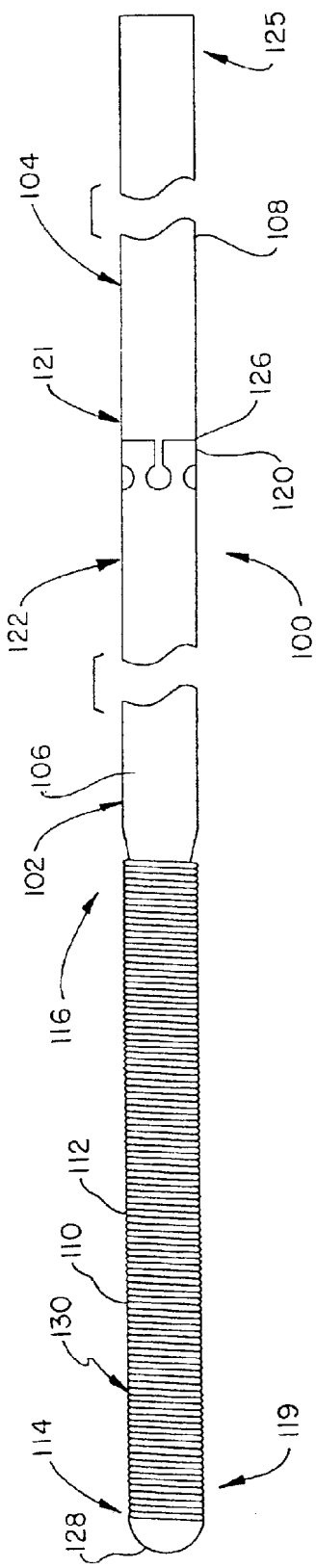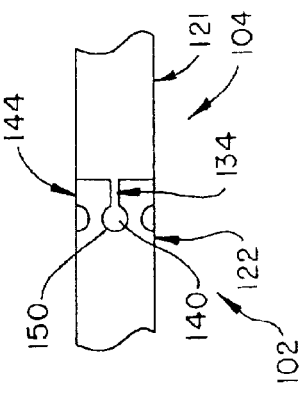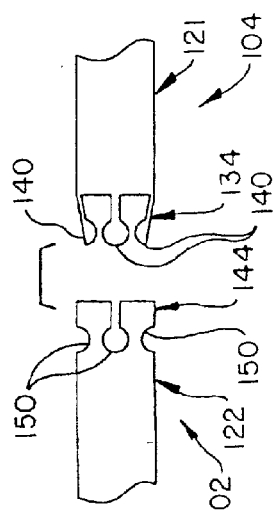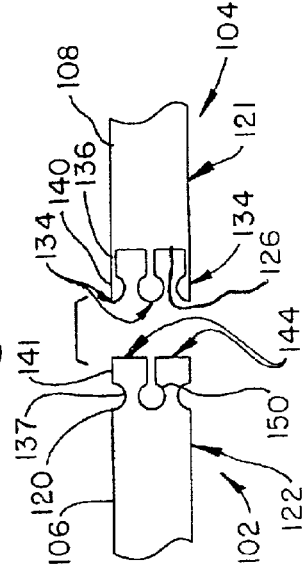

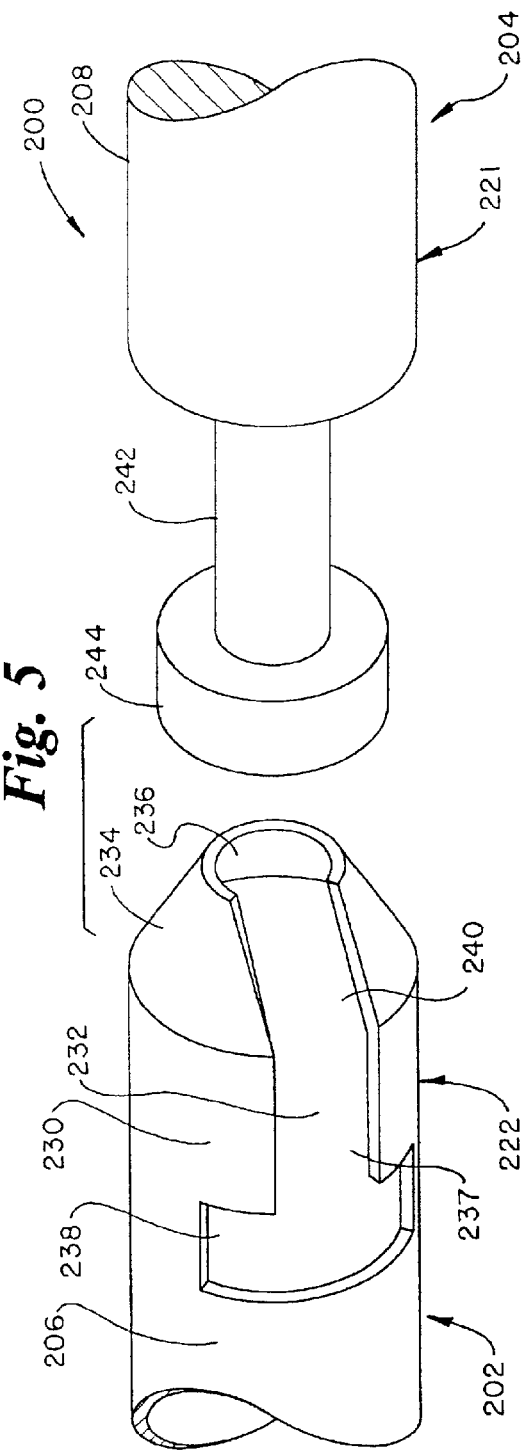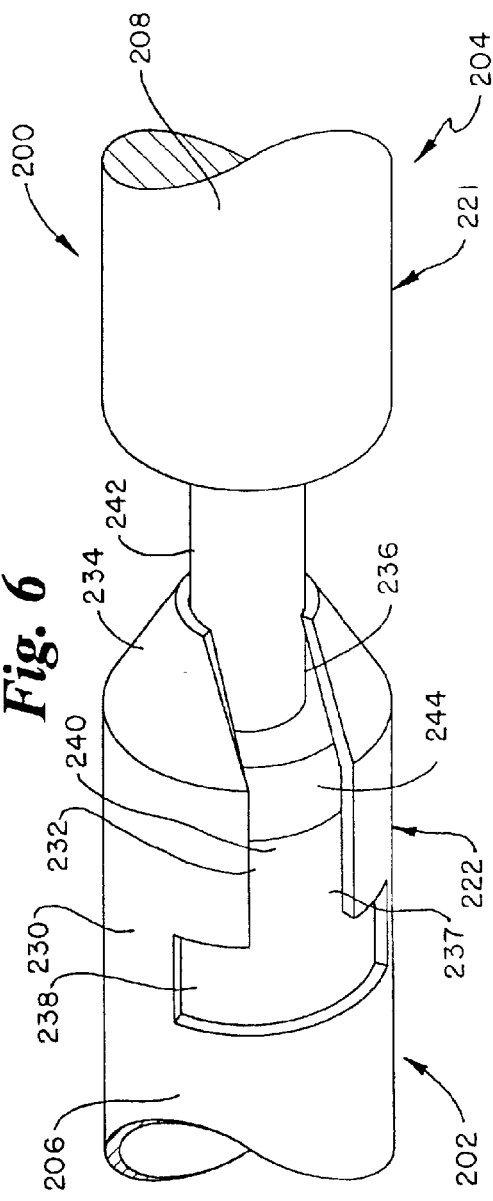

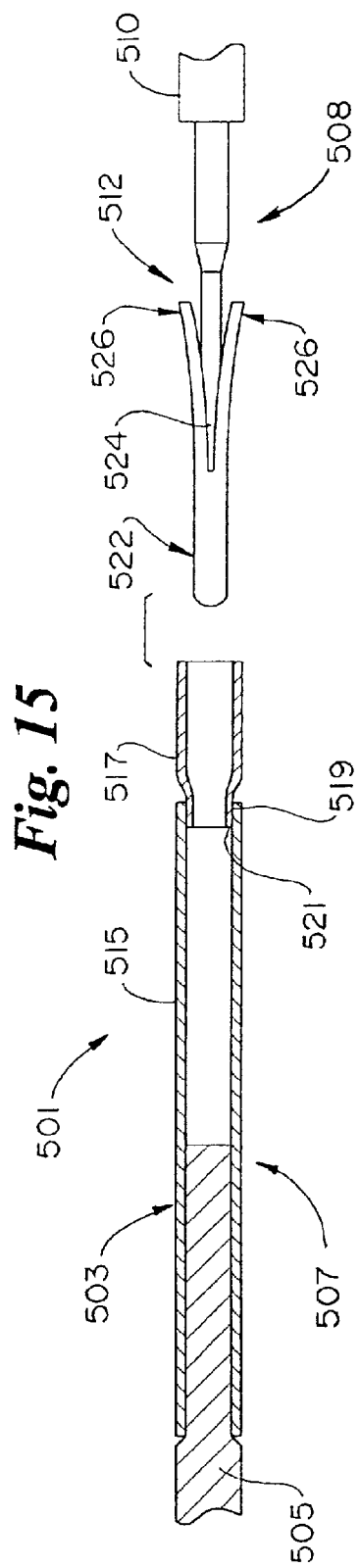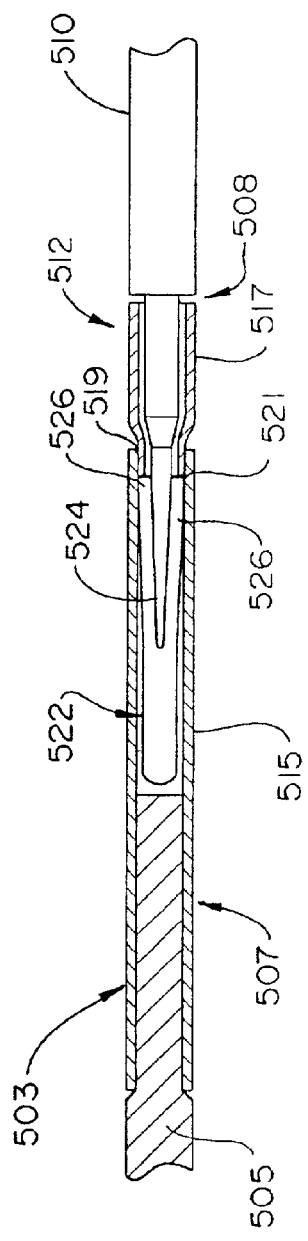

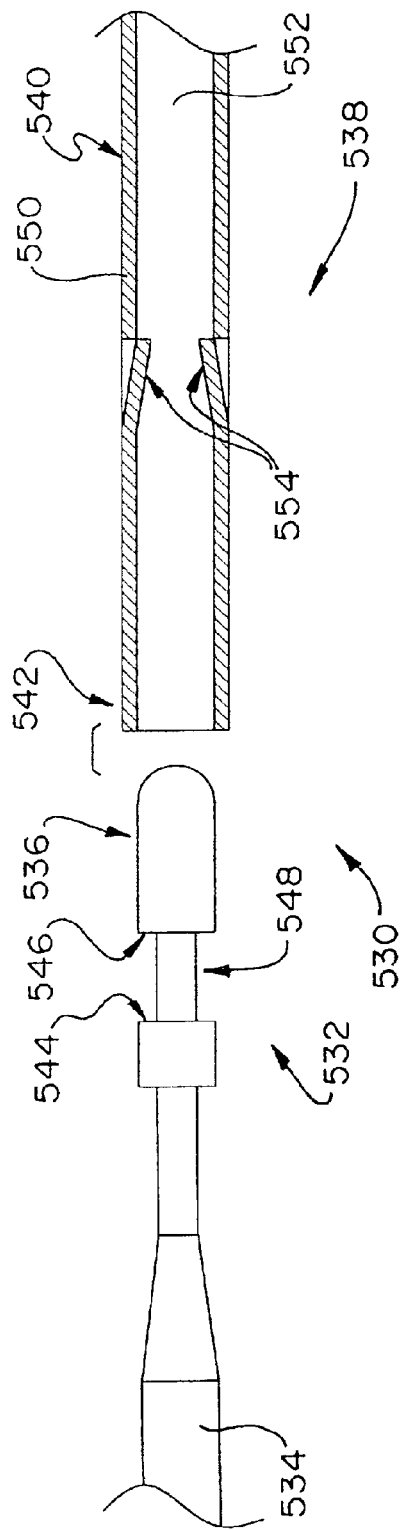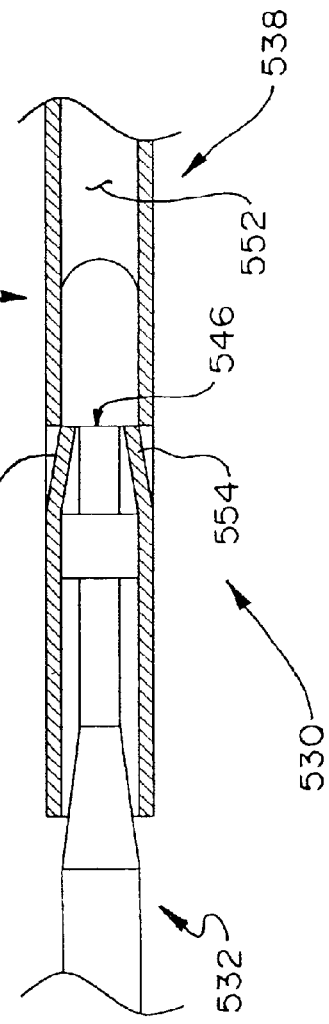

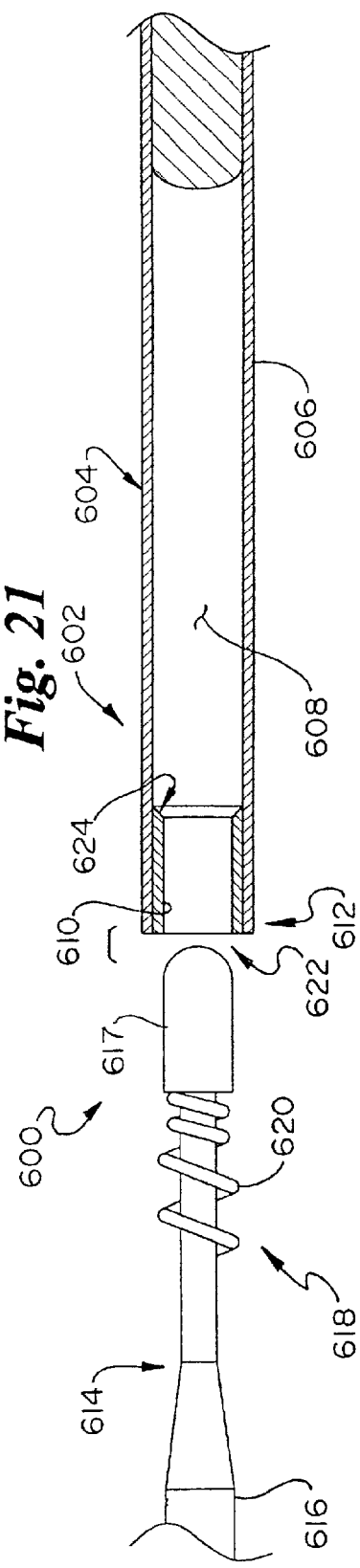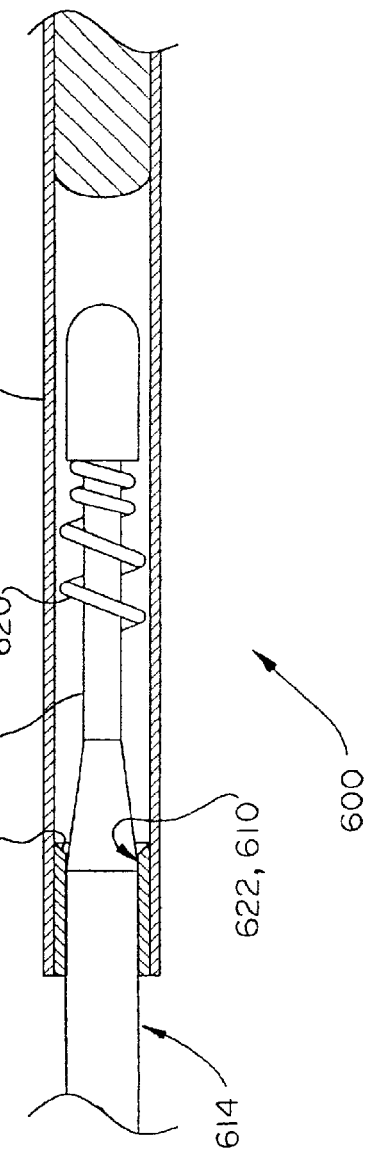

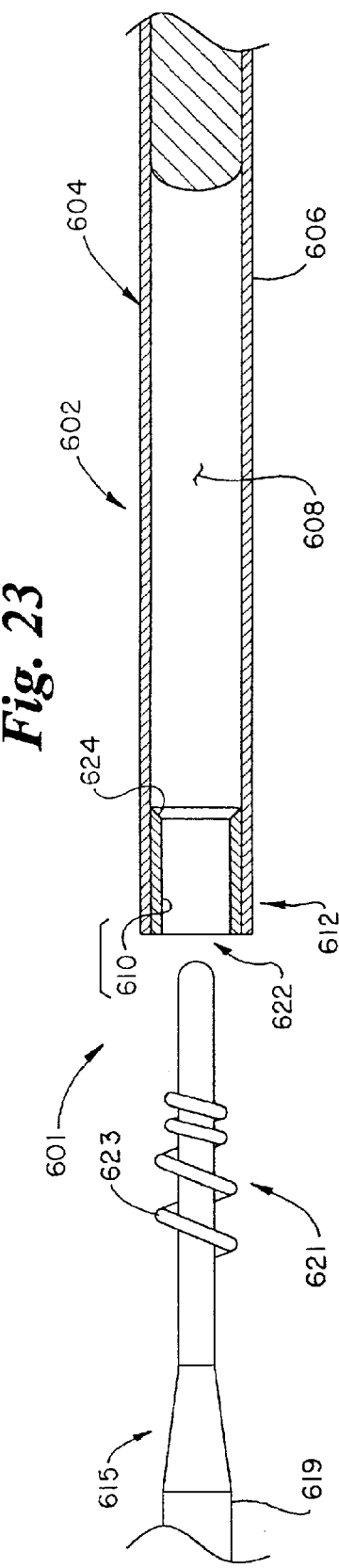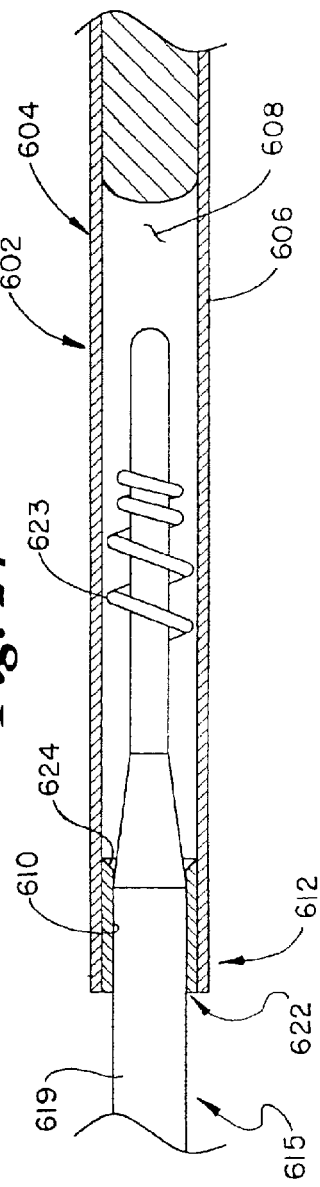

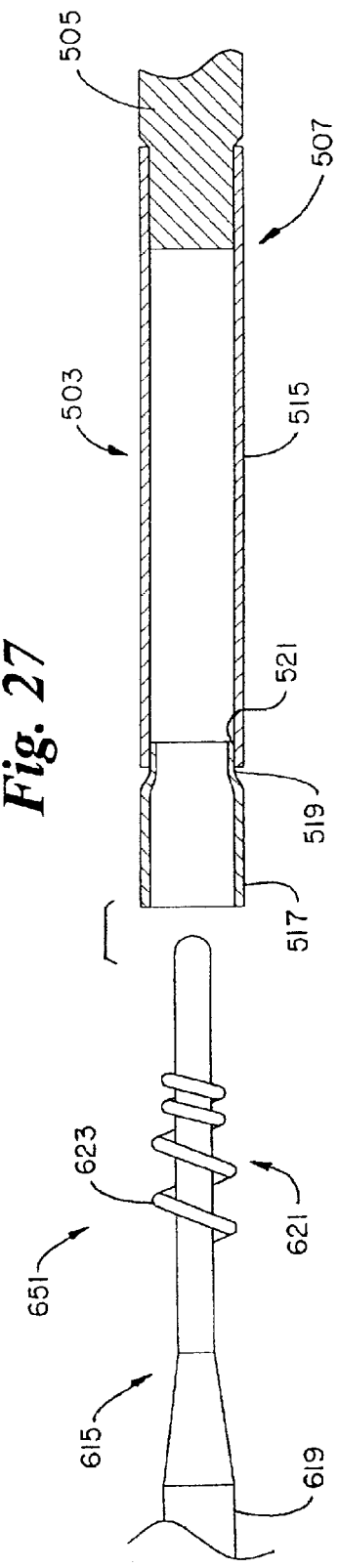
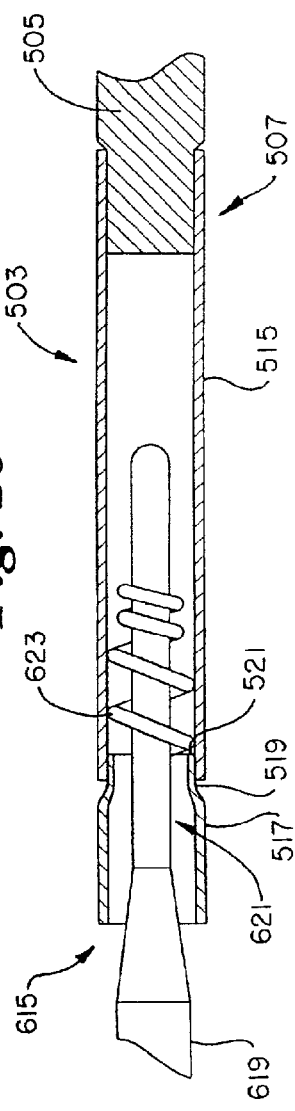

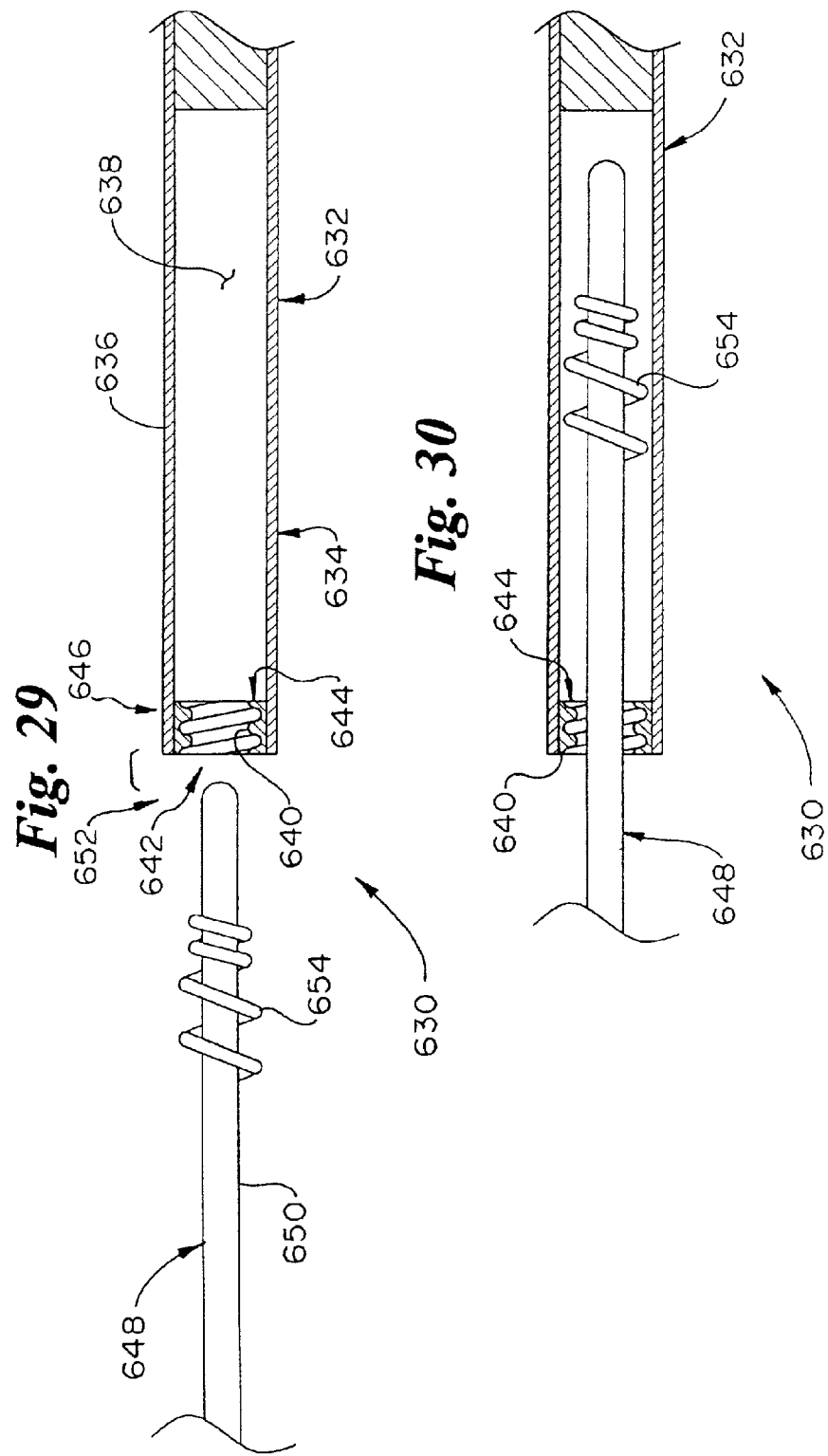

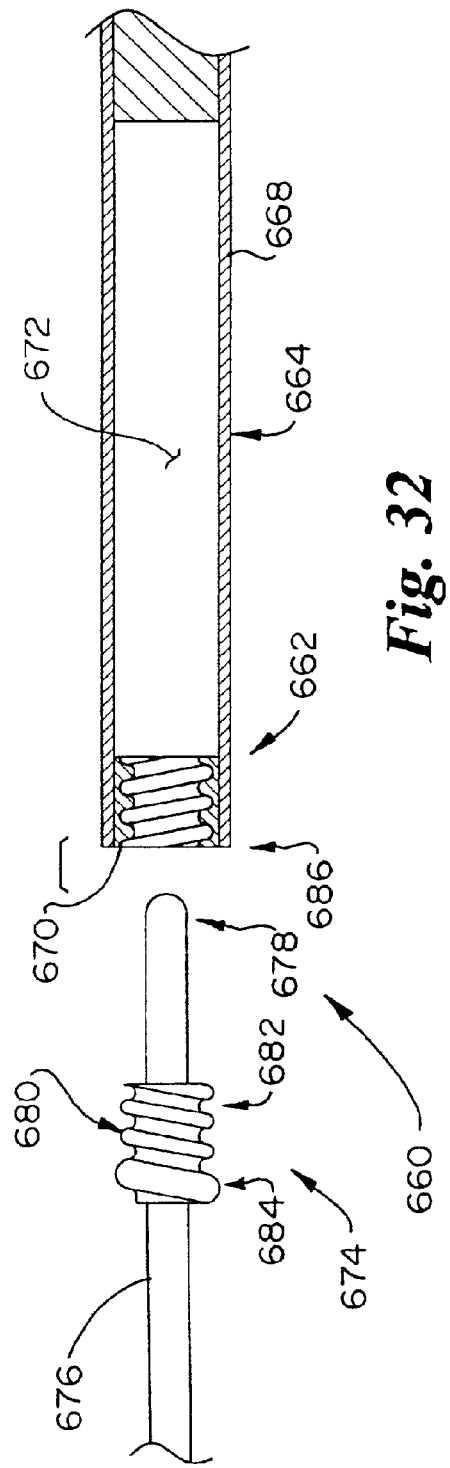
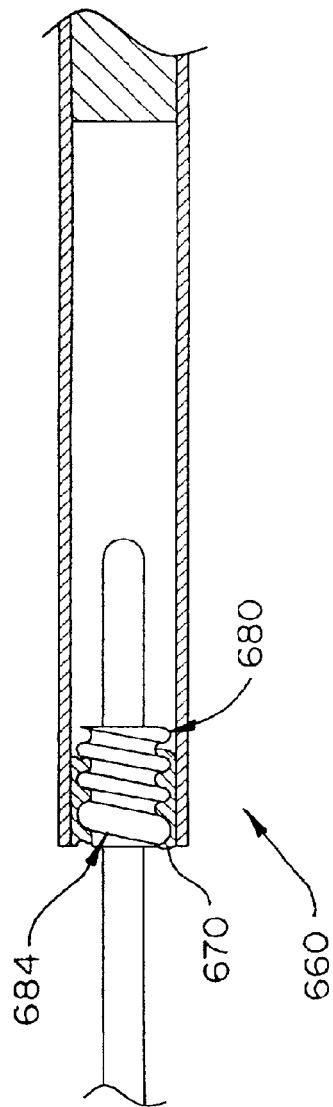
Fig. 31
Fig. 32

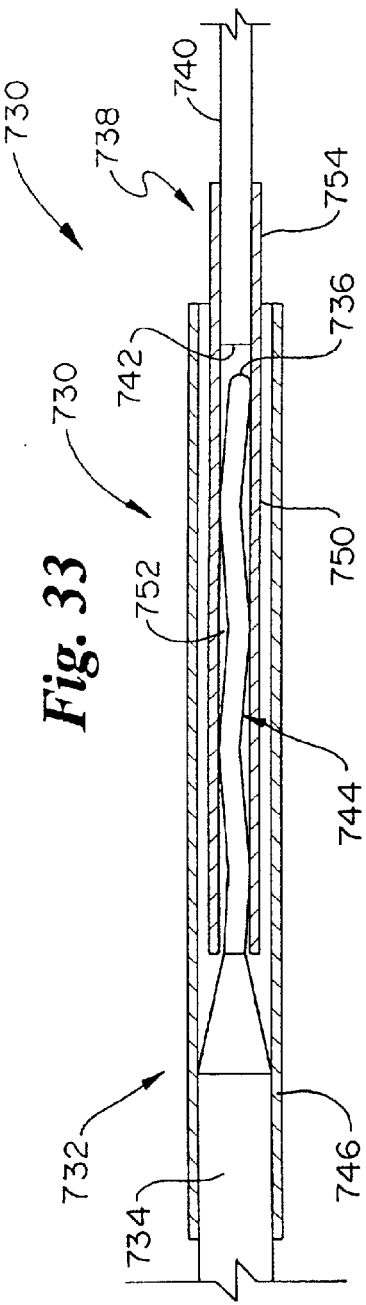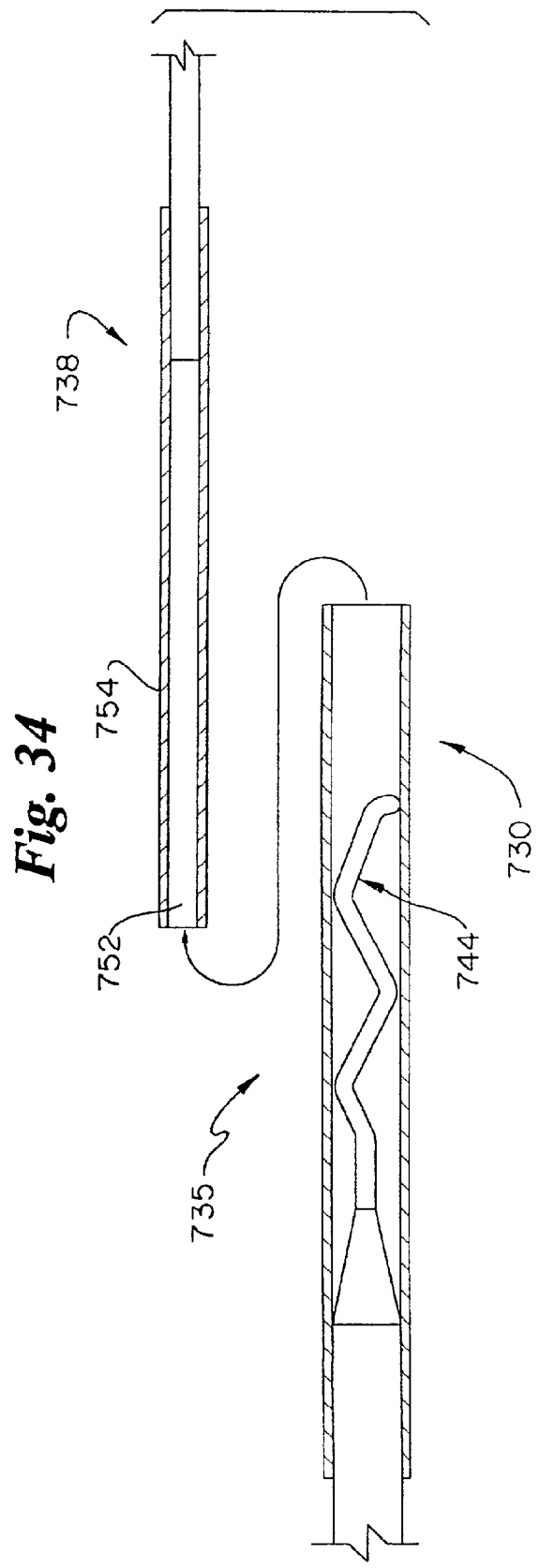
Fig. 33
Fig. 34

GUIDEWIRE EXTENSION SYSTEM

FIELD OF THE INVENTION

The invention relates generally to guidewires. More particularly, the invention relates to guidewire extension systems.

BACKGROUND OF THE INVENTION

Guidewires are currently utilized in a wide variety of medical procedures. In some situations, it would be desirable to provide a guidewire extension system to effectively extend the overall length of the guidewire.

In at least some cases, it would be desirable to provide an alternative extension system including an extension wire to be attached to the guidewire in a novel manner.

SUMMARY OF THE INVENTION

The invention is directed to guidewires, and in at least some embodiments, to guidewires for use in percutaneous surgical procedures. More particularly, the invention relates to guidewire extension systems. A guidewire system in accordance with the invention includes a first wire having a first end and a second wire having a second end which can be selectively coupled to the first end of the first wire.

BRIEF DESCRIPTION OF THE DRAWINGS

FIG. 1 is a partial plan view of a guidewire system in accordance with an exemplary embodiment of the invention;

FIG. 2 is an enlarged plan view having a first end portion of a first wire and a second end portion of a second wire of the guidewire extension system of FIG. 1;

FIG. 3 is an additional plan view of the first end portion of the first wire and the second end portion of the second wire of FIG. 2 showing the struts of the second wire being deflected inward;

FIG. 4 is an additional plan view of the first end portion of the first wire and the second end portion of the second wire of FIGS. 2 and 3, the first end portion of the first wire is coupled to the second end portion of the second wire;

FIG. 5 is a partial perspective view of another exemplary embodiment of a guidewire extension system showing a first end portion of a first wire and a second end portion of a second wire;

FIG. 6 is a perspective view of the guidewire extension system of FIG. 6, showing the first and second wire coupled together;

FIG. 15 is a partial cross sectional view of a portion of a guidewire system having a first wire and a second wire in accordance with yet another embodiment of the invention;

FIG. 16 is an additional partial cross sectional view of the guidewire system of FIG. 15, in which the first wire and the second wire are coupled together;

FIG. 17 is a partial cross sectional view of a portion of a guidewire system having a first wire and a second wire in accordance with yet another embodiment of the invention;

FIG. 18 is an additional view of the guidewire system of FIG. 17, in which the first wire and the second wire are coupled together;

FIG. 21 is a partial cross sectional view of a portion of a guidewire system having a first wire and a second wire in accordance with yet another exemplary embodiment of the invention;

FIG. 22 is an additional view of the guidewire system of FIG. 21, in which the first wire and the second wire are coupled together;

FIG. 23 is a partial cross sectional view of a portion of a guidewire system having a first wire and a second wire in accordance with yet another exemplary embodiment of the invention;

FIG. 24 is an additional view of the guidewire system of FIG. 23, in which the first wire and the second wire are coupled together;

FIG. 27 is a partial cross sectional view of a portion of a guidewire extension system having a first wire and a second wire in accordance with yet another exemplary embodiment of the invention;

FIG. 28 is a partial cross sectional view of the guidewire system of FIG. 27, wherein the first wire and the second wire are coupled together;

FIG. 29 is a partial cross sectional view of a portion of a guidewire extension system having a first wire and a second wire in accordance with yet another exemplary embodiment of the invention;

FIG. 30 is a partial cross sectional view of the guidewire system of FIG. 29, wherein the first wire and the second wire are coupled together;

FIG. 31 is a partial cross sectional view of a portion of a guidewire extension system having a first wire and a second wire in accordance with yet another exemplary embodiment of the invention;

FIG. 32 is a partial cross sectional view of the guidewire system of FIG. 31, wherein the first wire and the second wire are coupled together;

FIG. 33 is a partial cross sectional view of a portion of a guidewire system having a first wire coupled to a second wire in accordance with yet another embodiment of the invention;

FIG. 34 is an additional view of the guidewire system of FIG. 33, in which the first wire and the second wire are separated;

DETAILED DESCRIPTION OF THE INVENTION

Figure 7:
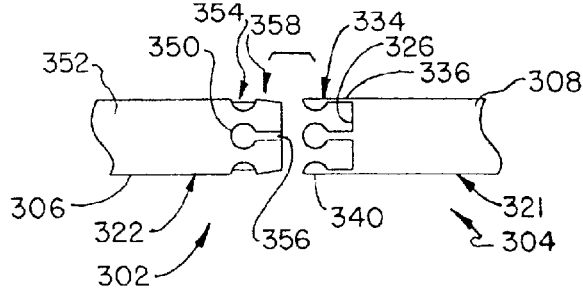
FIG. 7 is a plan view illustrating a first end portion of a first wire and a second end portion of a second wire which can form a portion of a guidewire extension system in accordance with another exemplary embodiment of the invention.

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

FIG. 1 is a plan view of a guidewire extension system 100 in accordance with an exemplary embodiment of the invention. Guidewire system 100 includes a first wire 102 and a second wire 104. First wire 102 comprises a body member 106 having a first end 120 and a second end 119. First wire 102 also includes a distal tip 128 fixed to body member 106 proximate second end 119.

A distal sheath 130 is disposed about body member 106 proximate second end 119. Preferably, the distal sheath 130 is generally fixed in position relative to the body member. In a preferred embodiment, one end portion 114 of distal sheath 130 is fixed to distal tip 128 and another end portion 116 of distal sheath 130 is fixed to body member 106 of first wire 102. Also in a preferred embodiment, distal sheath 130 has a high level of longitudinal pushability and a high level of lateral flexibility. Distal sheath 130 preferably comprises a coil 110 having a plurality of turns 112. Body member 106 of first wire 102 preferably has a generally cylindrical shape. Second wire 104 includes a body member 108 having a first end 125 and a second end 126. Second end 126 of second wire 104 is adapted and configured to be coupled to first end 120 of first wire 102.

FIG. 2 is a plan view illustrating first end portion 122 of first wire 102 and a second end portion 121 of second wire 104 in a non-coupled position. In FIG. 2, it can be appreciated that second wire 104 includes a plurality of struts 134 that extend beyond second end 126 of body member 108 of second wire 104. Each strut 134 includes a proximal portion 136 which is fixed to body member 108 proximate second end 126 and a generally enlarged portion 140.

First wire 102 includes a plurality of struts 144 which extend beyond first end 120 of body member 106 of first wire 102. Each strut 144 includes a proximal portion 137 which is fixed to body member 106 proximate first end 120 and a generally enlarged portion 141. Proximal portions 137 define a plurality of apertures 150. In a preferred embodiment, apertures 150 are sized to receive generally enlarged portions 140 of struts 134.

FIG. 3 is a plan view of the embodiment of FIG. 2 showing first end portion 122 of first wire 102 and second end portion 121 of second wire 104 and wherein struts 134 of second wire 104 have been deflected inward. In one method in accordance with the invention, struts 134 are deflected inward and second wire 104 is advanced toward first wire 102 until generally enlarged portions 140 of struts 134 are proximate apertures 150 defined by struts 144. Struts 134 of second wire 104 are then released so that they are free to return to an undeflected state. In this method, first wire 102 and second wire 104 may become fixed to each other by an intermeshing of struts 144 of first wire 102 and struts 134 of second wire 104.

FIG. 4 is a plan view of first end portion 122 of first wire 102 and second end 121 of second wire 104 of FIGS. 2 and 3. First wire 102 and second wire 104 are fixed to each other by an intermeshing of struts 144 of first wire 102 and struts 134 of second wire 104. Generally enlarged portions 140 of struts 134 are disposed within apertures 150 defined by struts 144.

FIG. 5 is a partial perspective view of another exemplary embodiment of a guidewire extension system 200. A first end portion 222 of a first wire 202 includes a body member 206 and a second end portion 221 of a second wire 204 includes a body member 208. The first end portion 222 includes a generally hollow tubular portion 230 defining a cavity 232 therein. The tubular portion 230 has a tapered end 234 defining an opening 236 in fluid communication with the cavity 232. The tubular portion 230 also defines an opening 237 in fluid communication with the cavity 232. Preferably, the opening 237 includes a wide portion 238 and a narrow portion 240 and is generally T-shaped. The narrow portion 240 is preferably in fluid communication with opening 236.

The second end portion 221, includes a recessed portion 242 and a wide portion 244 disposed on the end of the recessed portion 242. Preferably, the recessed portion 242 is generally annular in shape. The recessed portion 242 and the wide portion 244 together form structure 246 that is adapted and configured to mate with the tubular portion 230 to couple the first end portion 222 to the second end portion 221. The structure can be inserted into the cavity 232 through the opening 237. The wide portion 244 fits in to the wide portion 238, and the recessed portion 242 fits into the narrow portion 240.

Referring now to FIG. 6, once the structure 246 is within the cavity 232, the wide portion 244 is pulled toward the tapered end 234. The first and second wires are thereby selectively coupled together.

FIG. 7 is an enlarged partial plan view of another embodiment. This embodiment includes a first end portion 322 of a first wire 302 including a body member 306, and a second end portion 321 of a second wire 304 including a body member 308. The second wire 304 includes a plurality of struts 334 which extend beyond a second end 326 of body member 308 of second wire 304. Each strut 334 includes a proximal portion 336 which is fixed to body member 308 proximate second end 326 and a generally enlarged portion 340.

First wire 302 includes an outer surface 352 defining a plurality of apertures 350. Outer surface 352 preferably has a generally cylindrical shape, although other shapes are contemplated. Preferably, each aperture 350 is in fluid communication with a cavity 354 defined by body member 306 of first wire 302 but this is not necessary. Outer surface 252 of body member 306 of first wire 302 also defines a plurality of channels 356. Each channel 356 is preferably in fluid communication with a cavity 354. Each aperture 350 and its associated channel 356 form a generally keyhole shaped recess. In FIG. 7 it may be appreciated that body member 306 includes a tapered portion 358 proximate first end portion 322. Tapered portion 358 preferably has an outer diameter that is less than an outer diameter of struts 334. In some embodiments, at least a portion of the tapered portion 358 preferably has an outer diameter that is less than an inside diameter of a portion of struts 334.

Figure 8:
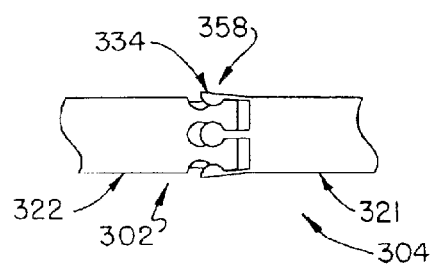
FIG. 8 is an additional plan view of the first end portion of the first wire and the second end portion of the second wire of FIG. 7 in a partially coupled position.
Figure 9:
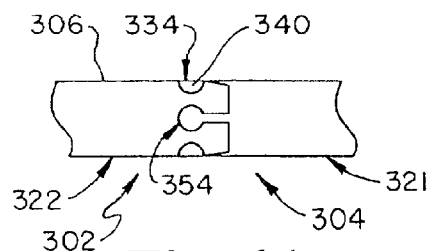
FIG. 9 is an additional plan view of the first end portion of the first wire and the second end portion of the second wire of FIGS. 7 and 8, in which the first end portion of the first wire is coupled to the second end portion of the second wire.

FIG. 8 is a plan view of the embodiment of FIG. 9, wherein the first end portion 322 of first wire 302 and second end portion 321 of second wire 304 have been urged toward one another and are partially coupled. Struts 334 of second wire 304 deflect outwardly as they ride upon an outer surface of tapered portion 358.

FIG. 9 is an additional plan view of FIGS. 7 and 8 wherein the first end portion 322 of first wire 302 and second end portion 321 of second wire 304 have been further urged toward one another and are coupled together. The generally enlarged portion 340 of each strut 334 of second wire 304 is disposed within a cavity 354 defined by body member 306 of first wire 302.

Figure 10:
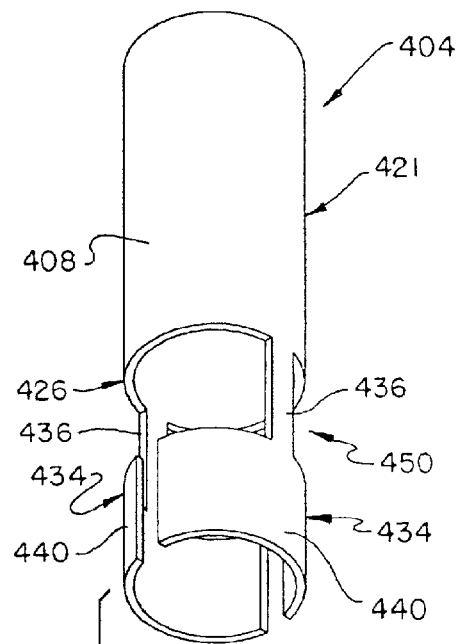
FIG. 10 is a partial perspective view of another exemplary embodiment of a guidewire extension system showing a first end portion of a first wire and a second end portion of a second wire.

FIG. 10 is a perspective view of yet another exemplary embodiment of a guidewire system 400. First end portion 422 of a first wire 402 and a second end portion 421 of a first wire 404 are shown. In FIG. 10, it can be appreciated that a body member 406 of first wire 402 defines a recess 460, a tapered end portion 458 and a plurality of channels 456. One channel 456 is visible in FIG. 10, and another channel (not visible in FIG. 10) is disposed generally opposite of the visible channel 456. The recess 460 has a generally annular shape.

The wire 404 includes struts 434 which extend beyond an end 426 of a body member 408 of wire 404. Each strut 434 includes a proximal portion 436 which is fixed to body member 408 proximate end 426 and a generally enlarged portion 440. Proximal portion 436 of struts 434 define a plurality of apertures 450.

Figure 11:
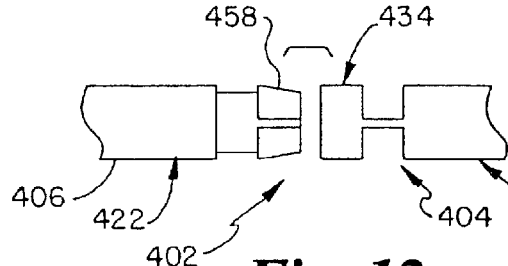
FIG. 11 is a plan view of a portion of the guidewire system of FIG. 10.

FIG. 11 is a plan view of a portion of the guidewire system 400 shown in FIG. 10. It can be appreciated that body member 406 of first wire 402 includes a tapered portion 458 proximate first end portion 422.

Figure 12:
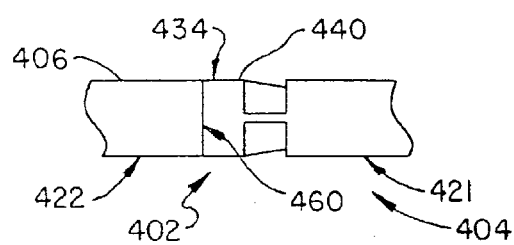
FIG. 12 is an additional plan view of the guidewire system of FIGS. 10 and 11 showing the wires coupled together.

FIG. 12 is a plan view of first end portion 422 of first wire 402 and a second end portion 421 of second wire 404 of FIG. 11 wherein the wires are coupled together. First end portion 422 of first wire 402 and second end portion 421 of wire 404 have been urged toward one another. A generally enlarged portion 440 of each strut 434 of wire 404 is disposed within the annular recess 460 defined by a body member 406 of first wire 402. Additionally, each proximal portion 436 of each strut 434 is disposed within one of the channels 456.

Figure 13:
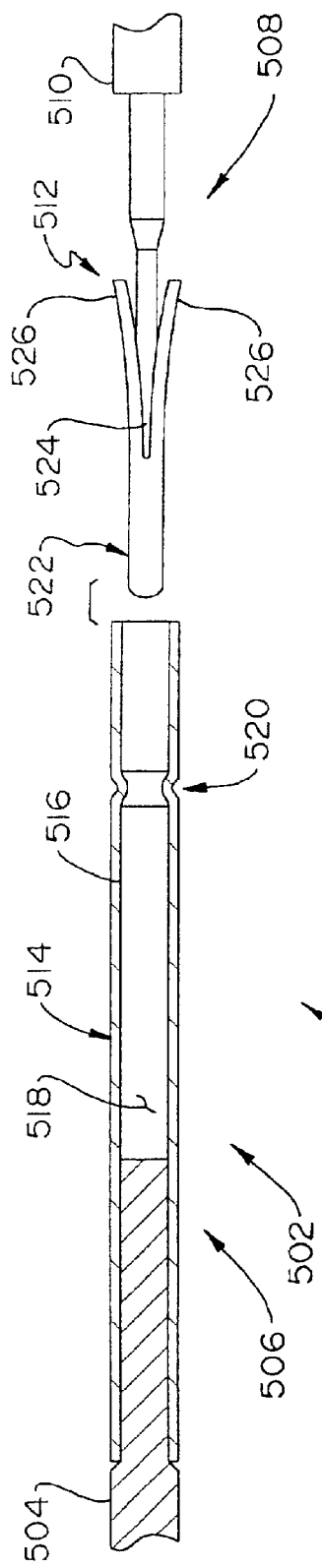
FIG. 13 is a partial cross sectional view of a portion of a guidewire system having a first wire and a second wire in accordance with yet another embodiment of the invention.

FIG. 13 is a partial cross sectional view of a portion of a guidewire system 500 in accordance with yet another embodiment of the invention. Guidewire system 500 includes a first wire 502 including a first body member 504 having a first end portion 506 and a second wire 508 including a second body member 510 having a second end portion 512. A first tubular member 514 is fixed to first body member 504 of first wire 502 proximate first end portion 506 thereof. First tubular member 514 includes a wall 516 defining a lumen 518 and a crimped portion 520 in which an inner diameter of wall 516 is generally reduced. A second tubular member 522 is fixed to second body member 510 of second wire 508 proximate second end portion 512 thereof. Second tubular member 522 defines a plurality of slots 524. Slots 524 define a plurality of fingers 526 of second tubular member 522. It can be appreciated that fingers 526 of second tubular member 522 are generally flared outward.

Figure 14:
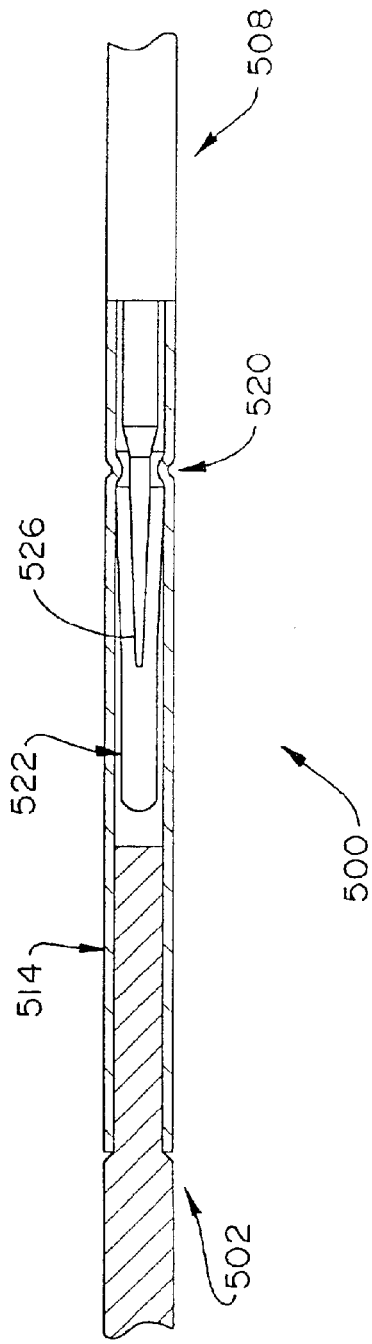
FIG. 14 is an additional partial cross sectional view of the guidewire system of FIG. 13, in which the first wire and the second wire are coupled together.

FIG. 14 is an additional view of guidewire system 500 of FIG. 13, wherein the second tubular member 522 has been inserted into first tubular member 514. It can be appreciated that fingers 526 of second tubular member 522 are adapted to seat against crimped portion 520 of first tubular member 514 to limit axial movement of second wire 508 relative to first wire 502. Embodiments of first tubular member 514 are possible in which a crimped portion 520 comprises a plurality of depressions. Embodiments of second tubular member 522 are possible in which slots 524 and fingers 526 have a generally helical shape.

FIG. 15 is a partial cross sectional view of a portion of a guidewire system 501 in accordance with yet another embodiment of the invention. Guidewire system 501 includes a first wire 503 including a first body member 505 having a first end portion 507 and a second wire 508. The second wire 508 is substantially the same as second wire 508 shown in FIGS. 13 and 14, with like reference numerals being used to identify like structures.

The first wire 503 includes a first tubular member 515 and a second tubular member 517 coupled to the body member 505 proximate the end portion 507 of first wire 503. The second tubular member 517 includes a narrow portion 519 that is adapted to fit within a portion of first tubular member 515 and forms an annulus within first tubular member. Narrow portion 519 includes an end surface 521.

FIG. 16 is an additional view of the guidewire system 501 of FIG. 15, wherein the tubular member 522 has been inserted into the tubular members 515 and 517 to couple the two wires 501 and 508 together. It can be appreciated that fingers 526 of the second wire 508 are adapted to seat against the end surface 521 of the first wire 508 to limit the axial movement of the wires 503 and 508 relative to one another.

FIG. 17 is a partial cross sectional view of a portion of a guidewire system 530 in accordance with yet another embodiment of the invention. Guidewire system 530 includes a first wire 532 including a first body member 534 having a first end 536. First body member 534 of first wire 532 includes a first surface 544 and a second surface 546 that define an annular cavity 548. Guidewire system 530 also includes a second wire 538 including a second body member 540 having a second end 542. Second body member 540 of second wire 538 includes a wall 550 defining a lumen 552 and a plurality of flaps 554 extending into lumen 552.

FIG. 18 is an additional view of the guidewire system 530 of FIG. 17 wherein the first end 536 of first wire 532 has been inserted into the lumen 552 of the second wire 538. The flaps 554 of second wire 538 are seated against second surface 546 of first wire 532. Flaps 554 and second surface 546 preferably limit axial movement of second wire 538 relative to first wire 532.

Figure 19:
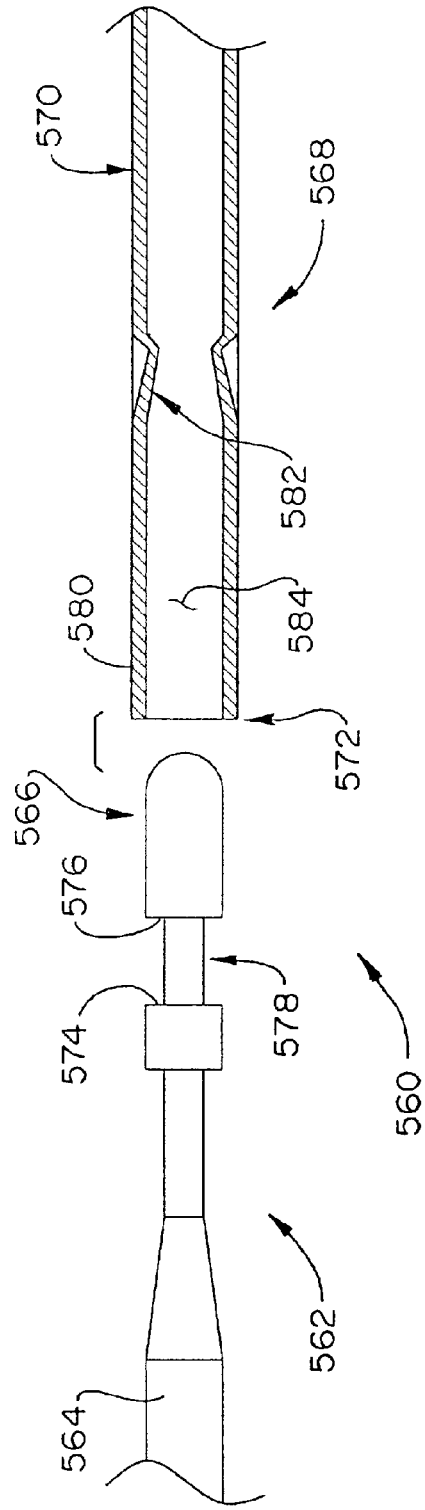
FIG. 19 is a partial cross sectional view of a portion of a guidewire system having a first wire and a second wire in accordance with yet another embodiment of the invention.

FIG. 19 is a partial cross sectional view of a portion of a guidewire system 560 in accordance with yet another embodiment of the invention. Guidewire system 560 includes a first wire 562 including a first body member 564 having a first end 566. First body member 564 of first wire 562 includes a first surface 574 and a second surface 576 that define an annular cavity 578. Guidewire system 560 also includes a second wire 568 including a second body member 570 having a second end 572. Second body member 570 of second wire 568 includes a wall 580 defining a lumen 584 and a plurality of arms 582 extending into lumen 584.

Figure 20:
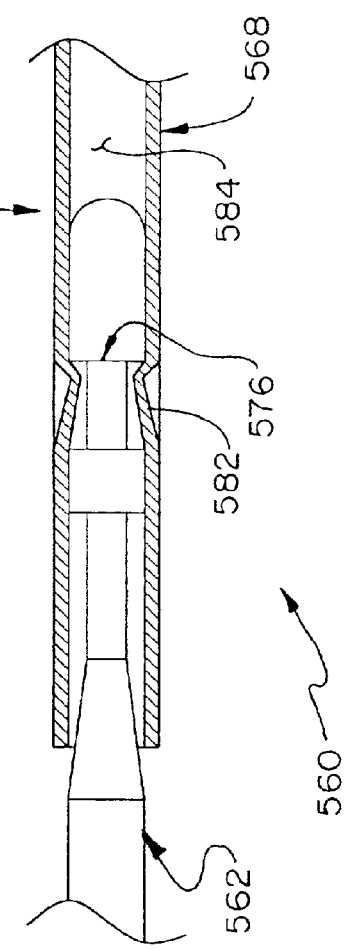
FIG. 20 is an additional view of the guidewire system of FIG. 19, in which the first wire and the second wire are coupled together.

FIG. 20 is an additional view of the guidewire system 560 of FIG. 19 wherein first end 566 of first wire 562 has been inserted into lumen 584 of second wire 568. The arms 582 of second wire 568 are seated against second surface 576 of first wire 562. Arms 582 and second surface 576 preferably limit axial movement of second wire 568 relative to first wire 562.

FIG. 21 is a partial cross sectional view of a portion of a guidewire system 600 in accordance with yet another embodiment of the invention. Guidewire system 600 comprises a first wire 602 including a first body member 604 comprising a wall 606 defining a lumen 608, and an annulus 610 disposed within lumen 608 proximate a first end 612 of first body member 604. Annulus 610 of first wire 602 defines an aperture 622 and a first surface 624. Guidewire system 600 also includes a second wire 614. Second wire 614 includes a second body member 616 having a second end 618. A coil 620 is disposed about second body member 616 of second wire 614 proximate second end 618 of second wire 614. Preferably, the coil 620 is maintained about second body member 616 by widening portion 617 proximate second end 618 of second wire 614. It will be understood, however, that the coil 620 can be maintained on the second body member in a broad variety of other ways.

FIG. 22 is an additional view of the guidewire system 600 of FIG. 21, wherein the second end 618 of second wire 614 has been inserted into aperture 622 of annulus 610 of first wire 602. It can be appreciated that coil 620 of second wire 614 may seat against first surface 624 of annulus 610 to limit axial movement of second wire 614 relative to first wire 602.

FIG. 23 is a partial cross sectional view of a portion of a guidewire system 601 in accordance with yet another embodiment of the invention. Guidewire system 601 comprises a first wire 602 that is substantially the same as the first wire 602 shown in FIGS. 21 and 22, and therefore includes a first body member 604 comprising a wall 606 defining a lumen 608, and an annulus 610 disposed within lumen 608 proximate a first end 612 of first body member 604. Annulus 610 of first wire 602 defines an aperture 622 and a first surface 624. Guidewire system 601 also includes a second wire 615. Second wire 615 includes a second body member 619 having a second end 621. A coil 623 is disposed about second body member 619 of second wire 615 proximate second end 621 of second wire 615. Preferably the coil 623 is maintained about second body member 619 of second wire 615 by attachment of at least a portion of the coil 623 to the body member.

FIG. 24 is an additional view of the guidewire system 601 of FIG. 23. In the embodiment of FIG. 24, second end 621 of second wire 615 has been inserted into aperture 622 of annulus 610 of first wire 602. It can be appreciated that coil 623 of second wire 615 can seat against first surface 624 of annulus 610 to limit axial movement of second wire 615 relative to first wire 602.

Figure 25:
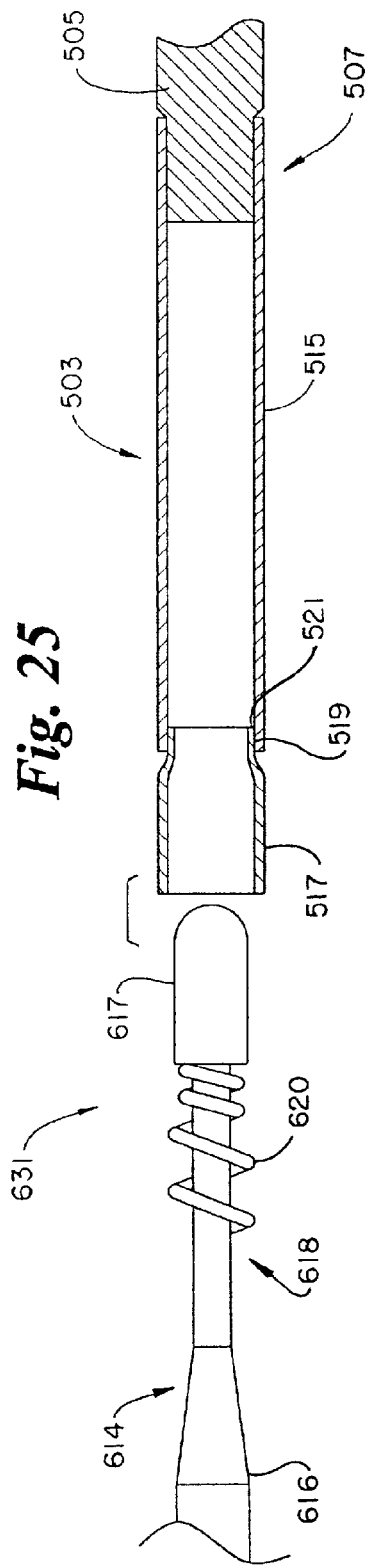
FIG. 25 is a partial cross sectional view of a portion of a guidewire extension system having a first wire and a second wire in accordance with yet another exemplary embodiment of the invention.

FIG. 25 is a partial cross sectional view of a portion of a guidewire system 631 in accordance with yet another embodiment of the invention. Guidewire system 631 comprises a first wire 503 that is substantially the same as the first wire 503 shown in FIGS. 15 and 16, and a second wire 614 that is substantially the same as the second wire 614 shown in FIGS. 21 and 22, with like reference numerals being used to identify like structure.

Figure 26:
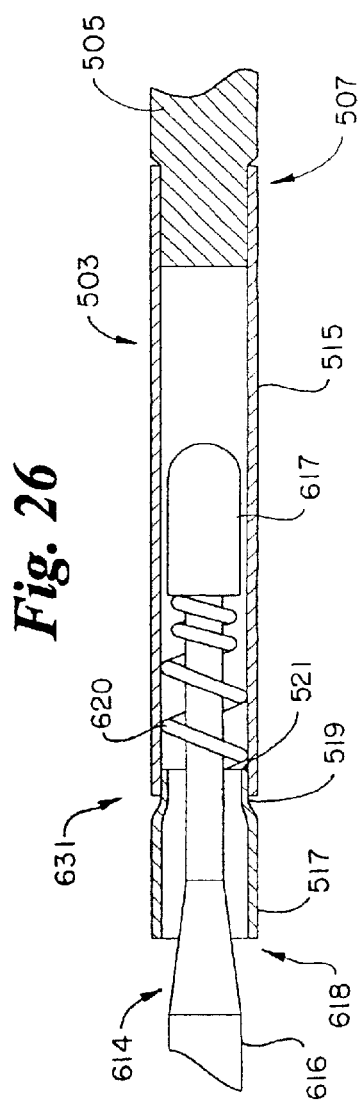
FIG. 26 is a partial cross sectional view of the guidewire system of FIG. 25, wherein the first wire and the second wire are coupled together.
Figure 35:
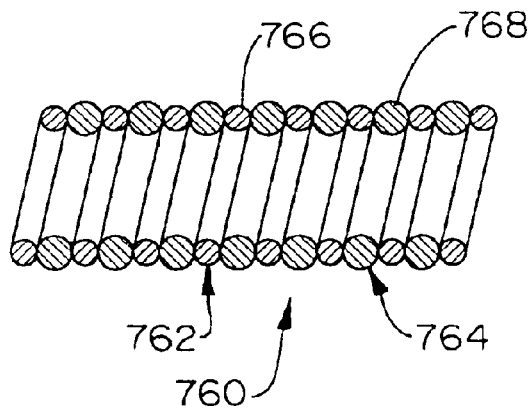
FIG. 35 is a partial cross sectional view of an exemplary embodiment of another invention disclosed herein relating to structure and methods of attaching a coil onto a tube or guidewire, showing an assembly including two different coils.
Figure 36:
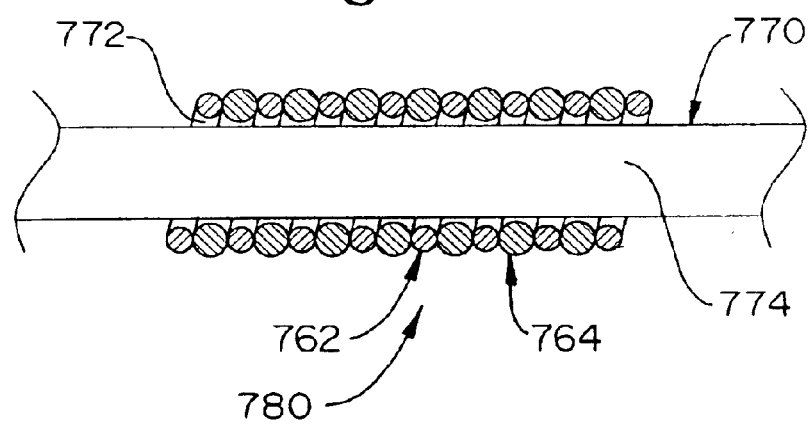
FIG. 36 is a partial cross sectional view of an assembly in accordance with the embodiment of FIG. 35, showing the coils disposed about a cylindrical member.
Figure 37:
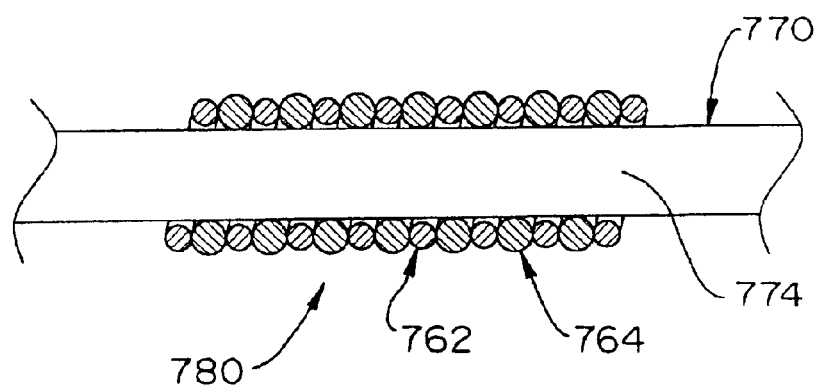
FIG. 37 is an additional view of the assembly of FIG. 30, showing the second coil tightened around the cylindrical member.

FIG. 26 is an additional view of the guidewire system 631 of FIG. 25, wherein the second end 618 of second wire 614 has been inserted into tubular members 515 and 517 to couple the wires 503 and 614 together. It can be appreciated that the coil 620 is adapted to seat against the end surface 521 of the first wire 503 to limit the axial movement of second wire 614 relative to first wire 503.

FIG. 27 is a partial cross sectional view of a portion of a guidewire system 651 in accordance with yet another embodiment of the invention. Guidewire system 651 comprises a first wire 503 that is substantially the same as the first wire 503 shown in FIGS. 15 and 16, and a second wire 615 that is substantially the same as the second wire 615 shown in FIGS. 23 and 24, with like reference numerals being used to identify like structure.

FIG. 28 is an additional view of the guidewire system 651 of FIG. 27, wherein the second end 621 of second wire 615 has been inserted into tubular members 515 and 517 to couple the wires together. It can be appreciated that the coil 623 is adapted to seat against the end surface 521 of the first wire 503 to limit the axial movement of second wire 615 relative to first wire 503.

FIG. 29 is a partial cross sectional view of a portion of a guidewire system 630 in accordance with yet another embodiment of the invention. Guidewire system 630 comprises a first wire 632 including a first body member 634 comprising a wall 636 defining a lumen 638, and a female thread 640 disposed within lumen 638 proximate a first end 646 of first body member 634. Female thread 640 of first wire 632 defines an aperture 642 and a first surface 644. Guidewire system 630 also includes a second wire 648. Second wire 648 includes a second body member 650 having a second end 652. A coil 654 is disposed about second body member 650 of second wire 648 proximate second end 652. Preferably, at least a portion of the coil 654 is rigidly attached to the body member 650.

FIG. 30 is an additional view of the guidewire system 630 of FIG. 29, wherein the coil 654 of second wire 648 has been threaded through female thread 640 of first wire 632. It can be appreciated that coil 654 of second wire 648 can set against first surface 644 of female thread 640 to limit axial movement of second wire 648 relative to first wire 632.

FIG. 31 is a partial cross sectional view of a portion of a guidewire system 660 in accordance with yet another embodiment of the invention. Guidewire system 660 comprises a first wire 662 and a second wire 674. First wire 662 includes a first body member 664 comprising a wall 668 defining a lumen 672, and a female thread 670 disposed within lumen 672 proximate a first end 686 of first body member 664. Second wire 674 includes a second body member 676 having a second end 678. A male thread 680 is disposed about second body member 676 of second wire 674 proximate second end 678 of second wire 674. Male thread 680 includes a first portion 682 which is adapted to threadingly engage female thread 670. Male thread 680 also includes a second portion 684 which is different from first portion 682 of male thread 680 (e.g., different pitch or different thread size). In a preferred embodiment of the invention, second portion 684 of male thread 680 is adapted to deform when male thread 680 is threaded into female thread 670.

FIG. 32 is an additional view of guidewire system 660 of FIG. 21, wherein the male thread 680 has been threaded into female thread 670. Also it can be appreciated that second portion 684 of male thread 680 has been deformed. The deformation of second portion 684 of male thread 680 preferably acts to reduce or prevent rotation of female thread 670 relative to male thread 680.

FIG. 33 is a partial cross sectional view of a portion of a guidewire system 730 in accordance with yet another embodiment of the invention. Guidewire system 730 includes a first wire 732 including a first body member 734 having a first end 736. First body member 734 of first wire 732 includes a zig-zag shaped tip portion 744. First wire 732 also includes a first tubular member 746 which is disposed about zig-zag shaped tip portion 744 and fixed to first body member 734. Preferably, zigzag shaped tip portion 744 is a bias-able, yet resilient material.

Guidewire system 730 also includes a second wire 738 including a second body member 740 having a second end 742 and a second tubular member 754 fixed to second body member 740 proximate second end 742. Second tubular member 754 of second wire 738 includes a wall 750 defining a lumen 752. The zigzag shaped tip portion 744 of first wire 732 is disposed within lumen 752 of second tubular member 754. The zig-zag shaped tip portion 744 may be inserted into lumen 752 of second tubular member 754 by straightening it under spring tension and advancing it.

FIG. 34 is an additional view of the guidewire system 730 of FIG. 33, wherein the first wire 732 and second wire 738 have been separated from one another. In FIG. 34 it can be appreciated that once zig-zag shaped tip portion 744 is removed from lumen 752 of second tubular member 754, it is free to return to an uncompressed position.

In some embodiments, guidewires as disclosed herein in accordance with the invention can be used in conjunction with an intravascular catheter that enables a physician to remotely perform a therapeutic medical procedure. Some examples of therapeutic purposes for catheters include percutaneous transluminal angioplasty (PTA), percutaneous transluminal coronary angioplasty (PTCA), the treatment of intracranial aneurysms in the brain and the like.

Guidewires are often utilized to assist in advancing the intravascular catheter through the vasculature of a patient. A guidewire may be inserted into the vascular system of the patient at an easily accessible location and urged forward through the vasculature until the tip of the guidewire is proximate the target site. A proximal end of the guidewire may then be inserted into a guidewire lumen of a catheter. The tip of the catheter may be advanced along the length of the guidewire until it reaches the target site.

It is sometimes necessary to remove one intravascular catheter and replace it with another. When this is the case, it is usually preferred that the first catheter be removed in a manner which enables the guidewire to remain in place in the blood vessel so that the second catheter can be inserted into the blood vessel over the guidewire. In order to maintain the position of the guidewire while withdrawing the first catheter, the guidewire typically must be gripped at its proximal end to prevent it from being pulled out of the blood vessel together with the catheter. The extension system of at least some embodiments of the invention allow an extension wire to be attached to a proximal end of the guidewire which is already in place in the body. This effectively extends the overall length of the guidewire to that needed for catheter exchange. Additionally, it is preferred that in most embodiments, the connection between the guidewire and the extension wire preferably presents low resistance to catheters that are passed over the connection.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A guidewire system, comprising:
   a first wire including a body member comprising a wall defining a lumen, and a female threaded member disposed within the lumen proximate a first end of the body member; and
   a second wire including a second body member having a second end, and a male thread adapted to threadingly engage the female thread of the first wire, the male thread being disposed about the body member of the second wire proximate the second end of the second wire;
   wherein the male thread includes a first portion and a second portion, wherein the second portion is more deformable than the first portion.

2. A guidewire system comprising:
   a first wire member including a body defining a lumen, and a female thread disposed within the lumen proximate an end of the first wire member; and
   a second wire member including body member having a male thread disposed about the body member proximate an end of the second wire member, the male thread adapted to threadingly engage the female thread and including a first portion and a second portion which is different from the first portion, the second portion being more deformable than the first portion.

3. The guidewire system of claim 2, wherein the deformation of the second portion of the male thread acts to inhibit rotation of the first member relative to the second member.

4. The guidewire system of claim 2, wherein the second portion of the male thread includes a different thread pitch from the first portion of the male thread.

5. The guidewire system of claim 2, wherein the second portion of the male thread includes a different thread size from the first portion of the male thread.

6. A guidewire system, comprising:
   a first wire having a first end;
   a second wire having a second end; and
   means for coupling the first end of the first wire to the second end of the second wire, the means including a female thread and a male thread adapted to threadingly engage, the male thread including a first portion and a second portion that is different from first portion and that is adapted to deform when threadingly engaged with the female thread.

* * * * *